(12) United States Patent
Thaler

(10) Patent No.: US 7,978,812 B2
(45) Date of Patent: Jul. 12, 2011

(54) COMPRESSION DEVICE FOR A MAMMOGRAPHY X-RAY APPARATUS

(75) Inventor: Phillip Thaler, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 152 days.

(21) Appl. No.: 12/369,496

(22) Filed: Feb. 11, 2009

(65) Prior Publication Data

US 2009/0213986 A1 Aug. 27, 2009

(30) Foreign Application Priority Data

Feb. 26, 2008 (DE) .......... 10 2008 011 154

(51) Int. Cl.
*A61B 6/04* (2006.01)
*H05G 1/02* (2006.01)

(52) U.S. Cl. .......... 378/37; 378/208

(58) Field of Classification Search .......... 378/37, 378/204, 208
See application file for complete search history.

(56) References Cited

U.S. PATENT DOCUMENTS

| 5,308,321 | A  | * | 5/1994  | Castro .......... 600/415 |
| 6,175,117 | B1 | * | 1/2001  | Komardin et al. .......... 250/363.06 |
| 6,254,614 | B1 | * | 7/2001  | Jesseph .......... 606/130 |
| 6,298,114 | B1 | * | 10/2001 | Yoda .......... 378/37 |
| 6,574,499 | B1 | * | 6/2003  | Dines et al. .......... 600/427 |
| 7,248,668 | B2 | * | 7/2007  | Galkin .......... 378/37 |
| 7,349,521 | B2 | * | 3/2008  | Al-Khalidy et al. .......... 378/37 |
| 7,489,761 | B2 | * | 2/2009  | Defreitas et al. .......... 378/37 |
| 7,742,796 | B2 | * | 6/2010  | Eberhard et al. .......... 600/407 |

FOREIGN PATENT DOCUMENTS

DE        40 37 387        5/1992

* cited by examiner

*Primary Examiner* — Allen C. Ho
(74) *Attorney, Agent, or Firm* — Schiff Hardin LLP

(57) ABSTRACT

A compression device for a mammography x-ray apparatus comprises the breast in a manner that is as comfortable as possible for the patient. For this purpose, a compression device has a frame that two-dimensionally stretches an elastic membrane and is designed so that the breast of a patient that is to be compressed by the compression device is compressed solely by the elastic membrane.

4 Claims, 3 Drawing Sheets

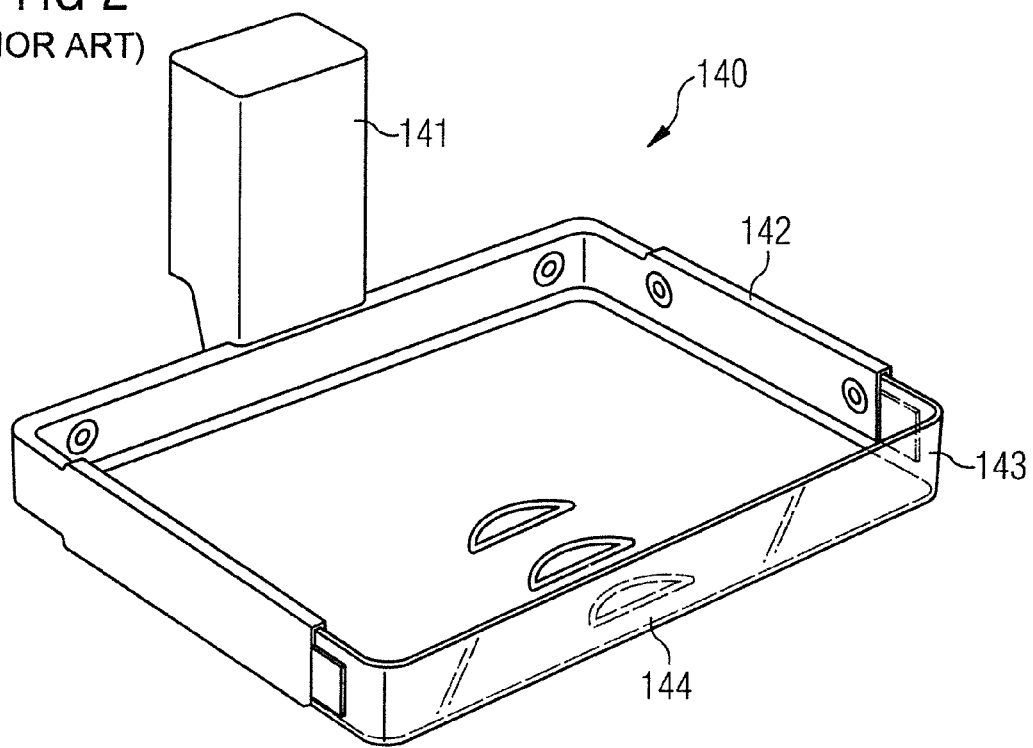

B-B

COMPRESSION DEVICE FOR A MAMMOGRAPHY X-RAY APPARATUS

BACKGROUND OF THE INVENTION

Field of the Invention

The present invention concerns a compression device for a mammography x-ray apparatus. In particular, the present invention concerns a compression device for mammography apparatuses in which the compression ensues in a comfortable manner for the patient.

Description of the Prior Art

As a radiology method, mammography is an x-ray examination of (typically) the female breast, but if necessary also of the male breast. Mammography is a method for early detection of breast cancer (mammary carcinoma), the most common cancer illness in women.

FIG. 1 shows a special x-ray apparatus 100 typically used for a mammography examination. The x-ray radiation emitted by an x-ray source 150 is a soft radiation in a range of approximately 23-35 kV. An image of the breast is acquired from each of two (most often above and laterally, at an angle) or more directions (tomography). During the acquisition, the breast is compressed between a table 130 and a compression plate 140 (most often made of Plexiglas®) in order to keep the radiation dose low and to "fan out" the tissue, i.e. to show more of the tissue, and in order to simultaneously avoid movement.

The actual acquisition apparatus has a radiation source 150, a compression plate 140 and table 130. The table 130 embodies a film mount/cassette mount in the case of analog x-raying, and an electronic sensor in the case of digital x-raying. The table 130 is connected with a support arm 120 which is connected in a height-adjustable manner with a column element 110. An articulation 125 can be optionally provided in order to support the acquisition apparatus so that it can rotate.

A conventional compression plate 140 is shown in FIG. 2. A frame 142 carries the actual plate 143 (frequently formed of Plexiglas®). An attachment element 141 is connected with the frame 142 and serves for the detachable and height-adjustable connection of the compression plate 140 to the acquisition apparatus. The plate 143 has a rounded leading edge 144 which is aligned toward the patient in the examination.

With this plate 143 the breast to be examined is pressed against the table 130, which is perceived as ranging from uncomfortable to painful, in particular along the edge 144 that compresses the largest circumference of the breast near the body of the patient.

SUMMARY OF THE INVENTION

An object of the present invention is to provide a compression device for mammography apparatuses in which the compression ensues as comfortable as possible for the patient.

This object is achieved by a compression device for a mammography x-ray apparatus with a frame that two-dimensional stretches an elastic membrane and is designed so that a breast of a patient that is to be compressed by the compression device is compressed only by the elastic membrane.

To intensify the compression pressure produced on the breast by the membrane, a negative pressure can be generated in the space formed between the elastic membrane (which is then air-impermeable), the breast and the table on which the breast lies.

In order to have control over the compression process at any time, in an embodiment a transparent membrane is used. The use of a membrane made from a non-adhering material (i.e., material that does not adhere to the breast) is additionally advantageous.

The invention also concerns a mammography x-ray apparatus with a compression device as described above.

An advantage of the present invention is that the compression is produced two-dimensionally and uniformly over the entire breast surface covered by the membrane, which is different than in the known, rigid compression plates,—and thus is perceived as less uncomfortable or less painful.

DESCRIPTION OF THE DRAWINGS

FIG. 2 shows a compression plate according to the prior art for use with an x-ray apparatus according to FIG. 1.

DESCRIPTION OF THE PREFERRED EMBODIMENTS

Figure 1:
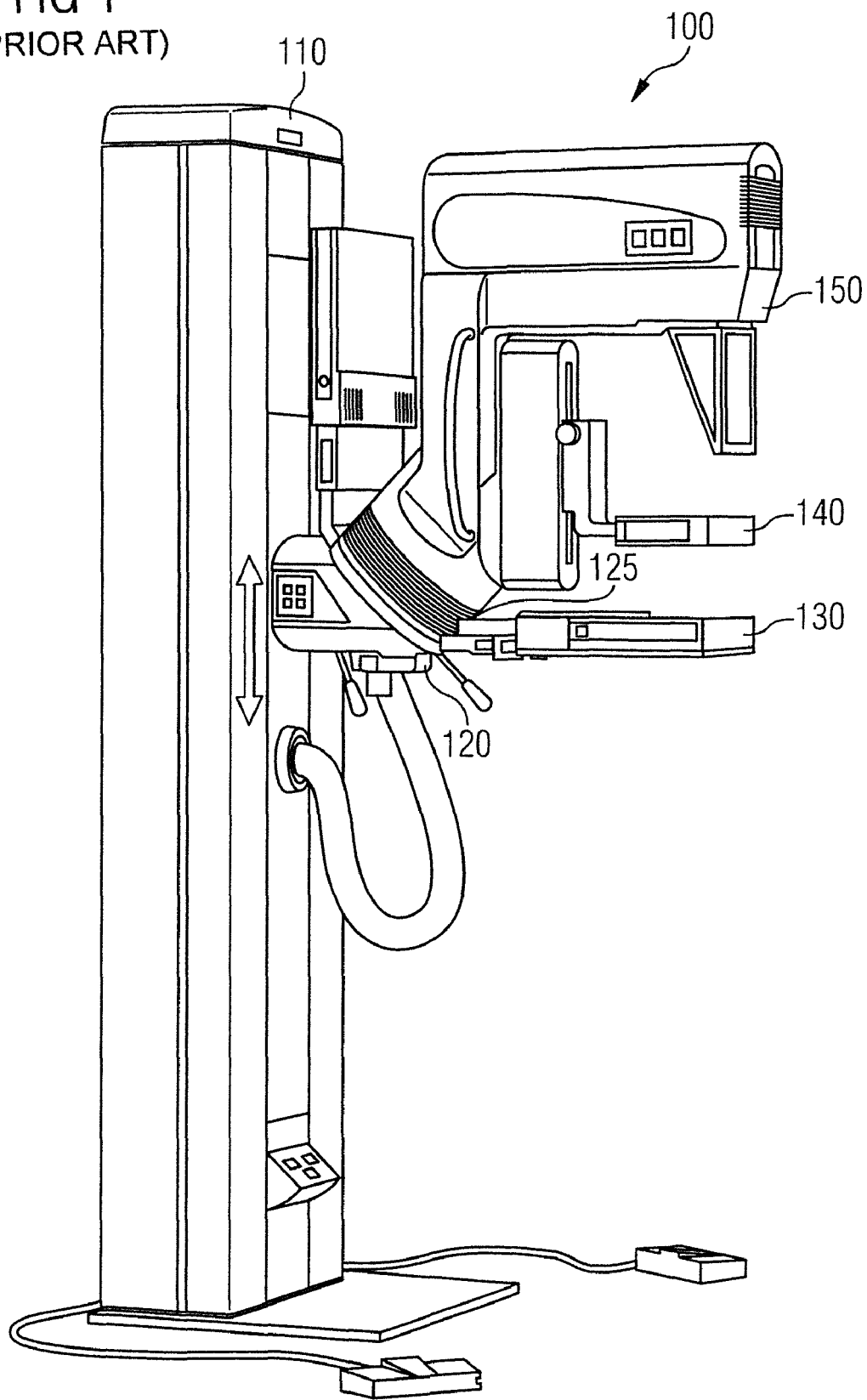
FIG. 1 illustrates a mammography x-ray apparatus.

FIG. 1 and FIG. 2 show a mammography x-ray apparatus 100 and a conventional compression plate 140. The details of FIG. 1 and FIG. 2 have already been described above.

Figure 3A:
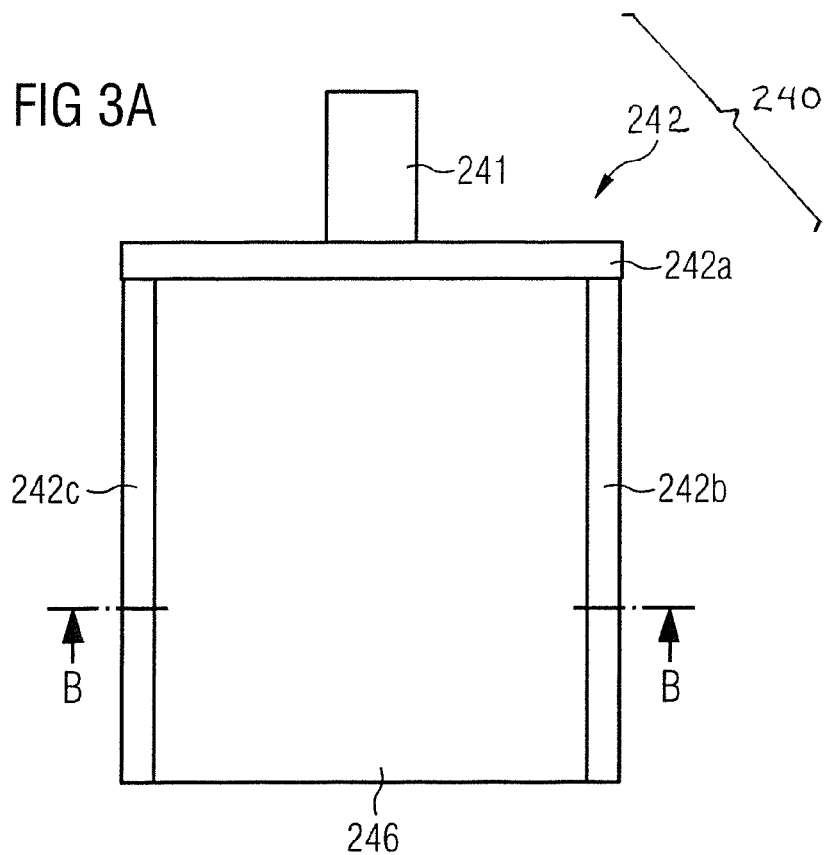
FIGS. 3A-3C respectively show various views of a compression device in correlation with an exemplary embodiment of the present invention.

FIG. 3A shows a compression device 240 according to the invention in a plan view, i.e. viewed from the radiation source 150 in the event that the compression device is mounted on an x-ray apparatus 100. The compression device 240 has an attachment element 241 connected to a frame 242 that is composed of frame parts 242a, 242b and 242c and that forms a right-angled U that is open in the direction of the patient. Instead of three frame parts, a frame 242 formed from one part can naturally also be provided. It is likewise possible to provide a rounded U-shape, a semi-circle or an arbitrarily different shape instead of the right-angled U-shape, as long as it is ensured that no frame part comes into contact with the breast to be examined during the compression process.

A flexible membrane 246 is fastened two-dimensionally on the frame 242 This membrane 246 covers the area spanned by the frame 242. This membrane 246 is preferably produced from elastic plastic and/or rubber and preferably has a thickness of 3-4 mm.

Figure 3B:
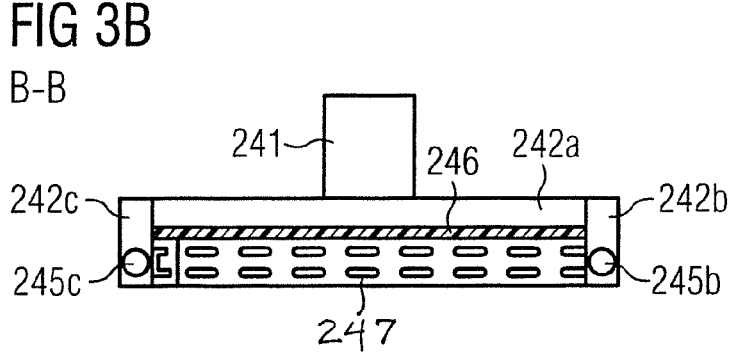
Figure 3C:
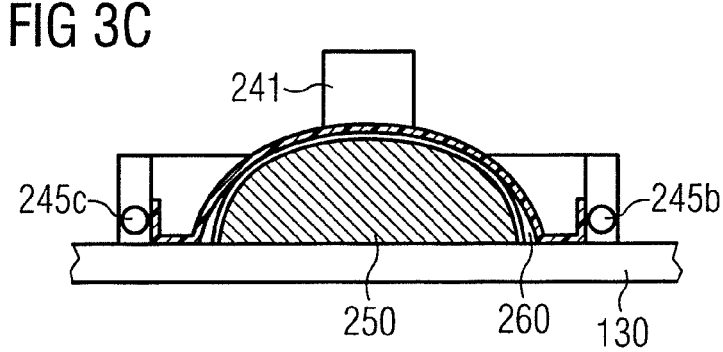

FIG. 3B shows the compression device 240 in section along section line B, and FIG. 3C shows the compression device 240 in an examination, likewise in section along section line B.

For an examination, the compression device 240 installed on a mammography x-ray apparatus 100 is lowered onto the table 130. The breast 250 (likewise shown in section) to be examined, which rests on the table 130 contacted solely by the membrane 246, is pressed by the membrane 246 onto the table 130 and is thereby compressed. In a first embodiment of the invention, the necessary compression is achieved with a sufficiently rigid membrane material, wherein the movement of the compression device toward the table ensues with a mechanical and/or electrical actuator (not shown) that is secured against unintentional reverse motion.

In another embodiment of the invention, the necessary compression is achieved by, after lowering the compression device 240 onto the breast 250 to be examined, pumping the air out from the space 260 remaining between the breast 250, the membrane 246 and the table 130, and thus the atmospheric pressure produces the compression of the breast 250. For achieving this suction, openings (not shown) can be provided on one side in the table, or respective channels 245*b* and 245*c* with openings 247 at the side of the membrane are provided in the frame parts 242*b* and 242*c*, through which channels 245*b* and 245*c* air is pumped. In order to achieve better results in the negative pressure generation, it may be necessary to provide a special seal (not shown) between the table 130 and the frame parts 242*a*, 242*b* and 242*c*, for example in the form of rubber lips fastened on the undersides of the frame parts.

Although modifications and changes may be suggested by those skilled in the art, it is the intention of the inventor to embody within the patent warranted hereon all changes and modifications as reasonably and properly come within the scope of his contribution to the art.

I claim as my invention:

1. A mammography apparatus comprising:

an x-ray source that emits an x-ray beam;

a support plate configured to support a breast thereon within said x-ray beam;

a radiation detector disposed to detect radiation in said x-ray beam after penetrating the breast on the support plate;

a compression device configured to compress the breast against said support plate, said compression device comprising a frame that defines an open frame interior and that is mounted for movement relative to said support plate, a non-rigid, elastic membrane that is impermeable to air and that has a membrane periphery and spanning said open frame interior and being attached to said frame only at said membrane periphery and being otherwise unhindered by said frame, said membrane and said frame forming an airtight space, and said frame being configured to two-dimensionally stretch said elastic membrane over and in conformity to the breast in order to compress the breast on the support plate solely by the elastic membrane;

said compression device comprising a negative pressure generator that generates a negative pressure in said space to intensify a compression pressure applied to the breast by the membrane.

2. A mammography apparatus as claimed in claim 1 wherein said membrane is comprised of transparent material.

3. A mammography apparatus as claimed in claim 1 wherein said membrane is comprised of non-adhering material.

4. A mammography apparatus as claimed in claim 1 wherein said membrane is comprised of transparent and non-adhering material.

* * * * *